United States Patent
Pauser et al.

(10) Patent No.: US 8,882,502 B2
(45) Date of Patent: Nov. 11, 2014

(54) DEVICE AND A METHOD FOR DELIVERY OF A DENTAL COMPOSITION

(75) Inventors: Helmut Pauser, Diessen (DE); Rüdiger Hampe, Landsberg (DE); Christoph Schulte, Windach (DE); Michael Knee, Peissenberg (DE); Andreas Maurer, Langenneufnach (DE)

(73) Assignee: 3M Innovative Properties Company, Saint Paul, MN (US)

( * ) Notice: Subject to any disclaimer, the term of this patent is extended or adjusted under 35 U.S.C. 154(b) by 531 days.

(21) Appl. No.: 12/996,680

(22) PCT Filed: May 29, 2009

(86) PCT No.: PCT/US2009/045655
§ 371 (c)(1),
(2), (4) Date: Mar. 3, 2011

(87) PCT Pub. No.: WO2009/151983
PCT Pub. Date: Dec. 17, 2009

(65) Prior Publication Data
US 2011/0151403 A1  Jun. 23, 2011

(30) Foreign Application Priority Data
Jun. 11, 2008 (EP) .................................. 08158033

(51) Int. Cl.
| | |
|---|---|
| *A61C 17/00* | (2006.01) |
| *A61C 17/02* | (2006.01) |
| *A61C 1/10* | (2006.01) |
| *A61C 9/00* | (2006.01) |
| *A61C 5/06* | (2006.01) |

(52) U.S. Cl.
CPC ............... *A61C 5/062* (2013.01); *A61C 9/0033* (2013.01)

USPC ............................................... 433/82; 433/80

(58) Field of Classification Search
USPC ................. 433/80, 82, 87–90, 215, 216, 136; 106/35; 523/116–118; 424/435, 434, 424/489; 401/181; 222/566–574, 326–327, 222/386–391
See application file for complete search history.

(56) References Cited

U.S. PATENT DOCUMENTS

| | | | |
|---|---|---|---|
| 4,384,853 A | * | 5/1983 | Welsh .............................. 433/90 |
| 4,763,791 A | | 8/1988 | Halverson et al. |

(Continued)

FOREIGN PATENT DOCUMENTS

| | | |
|---|---|---|
| DE | 37 37 552 | 11/1987 |
| EP | 1 402 873 | 9/2003 |

(Continued)

OTHER PUBLICATIONS

International Search Report for International Application No. PCT/US2009/045655, dated Jan. 18, 2010.

(Continued)

*Primary Examiner* — Yogesh Patel
(74) *Attorney, Agent, or Firm* — 3M Innovative Properties Company; Qiang Han

(57) ABSTRACT

A device for use in retracting a gingiva from a human tooth by widening a gingival sulcus with a dental composition. The device comprises a cannula with a free end having an opening for dispensing the dental composition. The free end is shaped to be inserted with its front in the entry of the gingival sulcus, and to laterally displace the gingiva from the tooth as the cannula is moved in the gingival sulcus. The invention may help to achieve a reliable and cost effective gingival retraction treatment.

4 Claims, 11 Drawing Sheets

(56) References Cited

U.S. PATENT DOCUMENTS

| | | | |
|---|---|---|---|
| 4,969,816 A * | 11/1990 | Drumm | 433/90 |
| 5,362,495 A | 11/1994 | Lesage | |
| 5,620,700 A | 4/1997 | Berggren et al. | |
| 6,135,771 A * | 10/2000 | Dragan et al. | 433/90 |
| 6,861,457 B2 | 3/2005 | Kamohara | |
| 7,053,135 B2 | 5/2006 | Schaub et al. | |
| 7,322,825 B2 | 1/2008 | Szymaitis | |
| 2005/0287494 A1 | 12/2005 | Yang | |
| 2006/0204924 A1 | 9/2006 | Galehr et al. | |
| 2007/0259313 A1 | 11/2007 | Dragan | |
| 2008/0125766 A1 | 5/2008 | Lubock et al. | |
| 2010/0092924 A1* | 4/2010 | Mongiorgi et al. | 433/228.1 |
| 2010/0183999 A1* | 7/2010 | Klettke et al. | 433/89 |

FOREIGN PATENT DOCUMENTS

| | | |
|---|---|---|
| EP | 1 639 022 | 8/2006 |
| EP | 1693022 | 8/2006 |
| JP | 2001-340363 | 11/2001 |
| JP | 312421 | 7/2006 |
| WO | WO 95/21731 | 8/1995 |
| WO | 2004/049965 | 6/2004 |
| WO | WO 2008/021740 | 8/2006 |

OTHER PUBLICATIONS

Silicates. *Ullmann's Encyclopedia of Industrial Chemistry*; vol. 32; Wiley-VCH: Weinheim, Germany, 2012; pp. 509-572.

\* cited by examiner

DEVICE AND A METHOD FOR DELIVERY OF A DENTAL COMPOSITION

CROSS REFERENCE TO RELATED APPLICATIONS

This application is a national stage filing under 35 U.S.C. 371 of PCT/US2009/045655, filed May 29, 2009, which claims priority to European Patent Application No. 08158033.4, filed Jun. 11, 2008, the disclosure of which are incorporated by reference in its/their entirety herein.

FIELD OF THE INVENTION

The invention relates to a device for use in retracting a gingiva from a human tooth, a method of retracting the gingiva from a human tooth, and a kit of parts which is adapted to perform such a method.

BACKGROUND ART

The restoration of a patient's tooth or teeth often includes the replacement of natural tooth structure by a manufactured dental restoration or dental prosthesis. Typically a tooth that is to be restored is first prepared by a dentist, for example by being abraded or ground to an appropriate shape to remove undesired tooth substance, and to provide the tooth with a shape appropriate to receive the dental restoration.

The dental restoration is typically mated precisely with the remaining tooth shape prepared by the dentist on the basis of an impression of the prepared tooth. Therefore the dental impression should be very precise, and should represent all tooth structure required to determine the shape of the mating surface of the later dental restoration. In particular the dental impression should represent the transition or the "margin" between the shape prepared in a tooth and the natural tooth shape. For dental restorations that extend below a patient's gingiva (or gums) the dentist also should make the part of the margin accessible for the dental impression that would normally be covered by the gingiva. The procedure of displacing the gingiva from the tooth to make the margin accessible is also known as "gingival retraction" in the field of dentistry. A common gingival retraction procedure includes the insertion of a so called retraction cord in the gingival sulcus. The gingival sulcus refers to an area between a tooth and the gingiva, as indicated for example in FIG. 1 at reference number 3.

One way of performing a gingival retraction procedure includes the use of a so-called gingival retraction cord which typically is pushed in the gingival sulcus to mechanically displace the gingiva from the tooth. A dentist may for example push a gingival retraction cord into the gingival sulcus by use of an appropriate dental instrument, for example by a Heinemann spatula. However, the insertion of a retraction cord (reference number 5, shown in FIG. 2) is relatively time consuming and is generally perceived as being relatively inconvenient for the dentist and uncomfortable for the patient. Therefore there has been a strong desire for viable alternatives for many years.

As an alternative for the retraction cord so-called gingival retraction pastes have been suggested. Typically retraction pastes are very high viscosity pastes which—instead of a cord—are typically squeezed in the gingival sulcus in a patient's mouth. In one example a paste is provided which is supposed to be brought into a patient's gingival sulcus to displace the gingival tissue from a tooth. A known paste is for example available under the designation Expasyl, from the company Pierre Roland, Acteon Group, France.

Such gingival retraction paste in one example is provided in a syringe that is connectable with a bendable metal dispensing cannula for dispensation of the paste. A technique has been proposed in which the high viscosity gingival retraction paste is dispensed around a tooth towards the entry of the gingival sulcus, and thereby is squeezed into the gingival sulcus. It has also been suggested to use auxiliary equipment for deeper insertion of the paste into the gingival sulcus in case the paste only has insufficiently penetrated the gingival sulcus during normal dispensation.

DE-A 37 37 552 discloses a composition for insertion into the gingival sulcus which is supposed to expand in volume and thereby to displace the gingiva from the tooth. The composition is intended to be injected into the gingival sulcus.

EP-A 1 693 022 discloses a process for gingival retraction. The process includes the application of an expanding and curing elastomeric material onto and/or the vicinity of the gingival sulcus, and restricting the expansion of the elastomeric material using a cap placed over the tooth. Pressure built up in the chamber due to the expansion of the elastomeric material is supposed to force the material into the gingival sulcus.

US2007259313 discloses a gingival tissue retraction device and method including a dam shaped to be fitted around a tooth. The well of the dam can be filled with a flowable retraction material having a high viscosity. The filled dam is fitted to a prepared tooth so that when pressure is applied onto the dam the retraction material is displaced under pressure and forced into the gingival sulcus, causing the gingival tissue to retract from the tooth.

WO 2008/021740 discloses a curable gingival retraction composition for retracting the gingiva from a tooth.

Although some developments particularly in the field of chemical compositions have been made, there is still a need for a procedure and a device allowing for convenient insertion of a composition for gingival retraction into the gingival sulcus. It is particularly desirable that a gingival retraction composition is made applicable in an acceptably short time, and with relatively little effort by the dentist. Further there is a need for a procedure that provides a treatment that is reliable, acceptable for a patient, and has few adverse side-effects or after-effects. Particularly a gingival retraction procedure desirably provides limited or low risk of damaging the epithelial attachment between the gingiva and the tooth. It is further desirable to provide a gingival retraction device and composition that are rather inexpensive and easy to use.

SUMMARY OF THE INVENTION

In a first aspect the invention relates to a device for use in retracting a gingiva from a human tooth. Particularly the first aspect of the invention relates to retracting the gingiva from the tooth by widening the gingival sulcus, formed between the gingiva and the tooth, with a dental composition.

The device of the invention comprises a cannula that has a free end which comprises an opening for dispensing the dental composition.

In one embodiment the free end and the opening are shaped so that the opening can be positioned to the entry of the gingival sulcus, with an outer lateral surface of the free end touching the tooth and the gingiva. The free end is further preferably shaped so that the gingiva is laterally displaced, for example predominantly laterally displaced, from the tooth as the cannula is further moved with the opening toward the inside of the gingival sulcus and/or as the free end of the cannula, when placed in the gingival sulcus, is moved along the margin around the tooth.

Thus the cannula preferably allows for injecting the dental composition in a pre-opened gingival sulcus which may help to reliably fill the gingival sulcus with the dental composition.

In another embodiment the free end has an outer lateral surface which extends between a first outer diameter D1 and a second outer diameter D2. Preferably the first outer diameter D1 is located adjacent the front of the free end, or at the front most end. The second outer diameter D2 is preferably located at a distance L2 further to the rear from the first outer diameter D1. D2 is preferably greater than D1. This preferably enables the device to displace the gingiva laterally away from the tooth, and preferably thereby enables the device to widen the gingival sulcus as the free end is moved farther into the gingival sulcus.

The term "diameter" may be generally interpreted as "cross-sectional dimension", for cases in which a non-circular cross-section is provided. For example instead of a circular cross-section, particularly for the opening of the cannula, an oval, rectangular (for example slit-shaped), star-shaped, or polygonal-shaped cross-section may be used.

The present invention may be advantageous for precisely injecting a dental composition in the gingival sulcus. Particularly the invention may help to keep the areas adjacent the entry of the gingival sulcus substantially free of the dental composition so that the entry of the gingival sulcus remains visible, for example by a dentist. The shape and dimensions of the cannula may help to avoid damage to the gingival tissue during use of the device of the invention in a patient's mouth. As another advantage the invention may reduce the risk of damaging the epithelial attachment. Furthermore the shape and dimensions in particular of the free end preferably facilitate insertion of the free end in the entry of gingival sulcus, and on the other hand allow the gingival sulcus to be widened for injecting the dental composition. The present invention may also be advantageous in dispensing the dental composition into the gingival sulcus in interproximal areas (between two teeth) in a patient's mouth. The invention also may allow the dental composition to be inserted relatively deep into the gingival sulcus, for example without increasing the force with which the material is dispensed. Deep penetration of the dental composition in the gingival sulcus may help to effectively retract the gingiva from a tooth, and consequently may help to provide an acceptable impression particularly of a preparation margin of a tooth. Further the invention may permit the use of dental compositions having a relatively high viscosity, which has been difficult in the past.

The diameter D1 may be between about 0.2 mm and about 1 mm, in particular between about 0.3 mm and about 0.7 mm, or between about 0.3 mm and about 0.8 mm, in more particular D1 may be within a range of about 0.4 mm to 0.6 mm. The diameter D1 is preferably about 0.4 mm. A relatively small dimension of the outer diameter D1 preferably allows, for example, the front of the free end to be inserted in the entry of the gingival sulcus relatively easily. Further such dimensions may help to reduce the risk of injuries of the gingival tissue during insertion of the front of the free end in the entry of the gingival sulcus, because it fits between the tooth and the gingiva rather than pressing on the gingiva itself.

The diameter D2 may be between about 0.6 mm and about 1.5 mm, in particular between about 0.9 mm and 1.4 mm, in more particular the diameter D2 may be between about 0.9 and 1.3 mm. Preferably the diameter D2 is about 1.1 mm, or more preferably about 1.0 mm. Such dimensions may for example provide the free end of the cannula with a sufficient stiffness, and on the other hand may still provide good interproximal access for the free end. Therefore the device of the invention may be suitable to inject a dental composition in the gingival sulcus all around a tooth in a controlled manner, and not only at distal or lingual portions of the gingival sulcus The length L2 of the free end may be between about 0.3 mm and about 2.0 mm, in particular between about 0.6 mm and about 1.5 mm, and preferably about 0.5 mm, or more preferably about 1 mm.

In another embodiment the first outer diameter D1 is located adjacent the opening. The first outer diameter D1 may also be formed by the opening. The opening may have a first inner diameter P1 which is between about 0.2 mm and 1 mm, however the opening may further have a first inner diameter P1 which is between about 0.3 mm and about 0.8 mm. In particular P1 may be within a range of about 0.4 mm to 0.6 mm, and preferably about 0.4 mm. P1 may be smaller than D1, but is preferably about equal to D1. In latter case P1 and D1 both refer to the diameter of the opening. In particular the inner diameter P1 may provide for the flow rate of a high viscosity dental composition to be controlled relatively precisely as the composition is injected into the gingival sulcus.

In another embodiment the lateral outer surface of the free end tapers from the second outer diameter D2 toward the first outer diameter D1. Thus, the taper preferably tapers in a direction from D2 toward D1. Furthermore the taper preferably tapers based on a curve having a relatively constant radius R. The Radius R may be greater than ½ of D2. For example, the shape of the free end may resemble a nose cone, a convex cone, or a radial cone. A curve resembling a radius greater than ½ of D2 may provide for a relatively low force required to insert the free end of the cannula in the entry of the gingival sulcus. Relative to a linear cone such convex or radial cone may further provide for a less blunt front-most end, which may reduce the risk of injuring the gingiva when inserted into the gingival sulcus.

The cannula of the device of the invention may have a length L1 between the first outer diameter D1 and a third outer diameter D3. The cannula may have a shaft portion extending between the second outer diameter D2 and the third outer diameter D3. The shaft portion and the free end may be located adjacent to each other, and together extend along the length L1. The third outer diameter D3 may be between about 0.6 mm and about 2.5 mm, in particular between about 0.9 mm to about 1.9 mm, and preferably about 1.8 mm. D3 is preferably greater than D2, but may also be about equal to D2. Thus, the shaft portion may be generally cylindrical or conical. Preferably the shaft portion smoothly transitions to the free end. The length L1 may be between about 4 mm and about 18 mm, in particular between about 6 mm and about 14 mm, and preferably about 11 mm. Such dimensions preferably allow the cannula to access areas that are accessible only through narrow spaces in a patient's mouth, for example a gingival sulcus between two teeth. This may also help in injecting a dental composition around substantially the entire perimeter of a tooth.

In one embodiment the cannula has a marking. The marking preferably is usable as reference with regard to a certain (for example a preferred) penetration depth of the cannula in the gingival sulcus. The marking may help a user to observe and/or to assess the depth to which the cannula is inserted in the gingival sulcus during a treatment of a patient. Therefore a user may control the penetration depth of the cannula relatively precisely and thereby may achieve an effective gingival retraction. On the other hand this may help to avoid damage to the gingival tissue which may result from too deep penetration of the cannula in the gingival sulcus. The marking may be a notch, a rim, a step, or a (printed) line, for example. The marking may extend partly or entirely circumferentially around the cannula. The marking may further be formed by a transition between colors of outside surfaces of the cannula. For example, the front end of the cannula may have a certain first outside color, and an adjacent rear portion of the cannula may have a certain second outside color, wherein the first and second colors are different. The marking may also be formed by a transition between areas of different transparency or translucency. Preferably the marking is formed by a transition between surface structures of outside surfaces of the cannula. For example, the front end of the cannula may have a generally even or glossy outside surface, and an adjacent rear portion of the cannula may have a more rough or matt outside surface. The marking may also be a scale marking different penetration depths.

A second aspect of the invention is related to the device of the invention in combination with a dental impression material, and a third aspect of the invention is related to the device of the invention in combination with a gingival retraction material.

The dental impression material is preferably characterized in that it comprises an alginate, or a synthetic elastomeric impression material selected from a polyether, a silicone and mixtures thereof, for example a silicone containing polyether group. The dental impression material may further comprise polysulfides, condensation cured silicones, addition cured silicones, and mixtures of those.

In one embodiment the device of the invention contains a self-hardening dental impression material. For example a user may mix such a self-hardening dental from at least two components outside of the device of the invention and fill the device with the mixture which then hardens or cures within a time period (for example within a time period of less than 20 minutes).

An exemplary embodiment of a dental impression material comprises organopolysiloxane containing unsaturated hydrocarbons and polyether containing unsaturated hydrocarbons and a silicone soluble platinum compound as disclosed in U.S. Pat. No. 6,861,457. Another exemplary embodiment of a dental impression material comprises a silicon functionalized polyether derivative containing an antacid component as disclosed in EP 1 402 873.

In one embodiment the device of the invention contains a gingival retraction material which comprises a liquid and a silicate filler. The group of silicate minerals typically includes, inter alia, silicon dioxides (also named silica), quartz, and phyllosilicates.

In another embodiment the device of the invention contains a gingival retraction material which comprises a liquid and a combination of at least two different phyllosilicates.

"Phyllosilicates" are silicates forming sheets of silicate tetrahedra with $Si_2O_5$. Phyllosilicates can be further divided in sub-groups, e.g. according to the number of sheets or layers arranged with each other. Phyllosilicates are divided for purposes of the present invention into the following subgroups: silicate minerals of the 2:1 layer type group and silicate minerals of the 1:1 layer type group. With respect to this classification a more detailed description can be found in Ullmanns Encyclopedia of Industrial Chemistry (Wiley-VCH), 2005, Silicates; table 4. According to this reference, clay minerals belong to the group of phyllosilicates and can be characterized by the number of layers linked or arranged with each other. This classification is also used with respect to the present invention. For example in kaolinite, having the ideal formula $Al_2[Si_2O_5(OH)_4]$, two single layers are linked or arranged with each other. For example in muscovite, having the ideal formula $KAl_2(AlSi_3O_{10})(OH)_2$ and belonging to the Mica type group of minerals, three layers are linked or arranged with each other.

The combination of phyllosilicates may comprise a layer type 1:1 silicate mineral and a layer type 2:1 silicate mineral in a certain ratio relative to each other. Phyllosilicates from the layer type 1:1 silicate mineral which can be used include kaolinite, lizardite and mixtures or combinations thereof, wherein kaolinite is preferred. Phyllosilicates from the layer type 2:1 silicate minerals which can be used include talc-pyrophyllite type minerals, smectite type minerals, vermiculite type minerals, illites type minerals, mica type minerals and mixtures and combinations thereof. Specific examples include talc, willemseite, pyrophyllite, stevensite, saponite (from the talc-pyrophyllite type group of minerals), sponite, sauconite, hectorite, montmorillonite, beidellite, nontronite, volkonskite (from the smectite type group of minerals), phlogopite, biotite, lepidolite, muscovite, illite, glauconite, celadonite (from the mica type group of minerals).

The layer type 1:1 silicate mineral and the layer type 2:1 silicate mineral are typically present in the gingival retraction material in a certain weight ratio with respect to each other. This weight ratio includes a range from about 50/50 to about 5/95 or from about 30/70 to about 10/90. That is, the content of the layer type 1:1 silicate mineral and the content of the layer type 2:1 silicate mineral in the gingival retraction material can be about equal. It is, however, also within the scope of the invention that the layer type 2:1 silicate mineral is present in excess compared to the layer type 1:1 silicate mineral. If the ratio is within the above mentioned ranges, the resulting gingival retraction material is advantageous in that it tends to require a low extrusion force, but may have a relative good storage modulus. Further such a gingival retraction material may be removable from a patient's mouth relatively quickly, for example by rinsing with water.

Liquids suitable for preparing the gingival retraction material include those which are generally able to form a paste or gel with the other components present. In particular the liquids may include polar and non-polar liquids and mixtures thereof. Specific examples include water, alcohols (e.g. ethanol, n- and iso-propanol, erythritols), ketons (e.g. acetone), glycerine (e.g. ethoxylated glycerin), glycols (e.g. ethyleneglycol, propyleneglycol and/or its oligo or mixed oligomers) and silicon oils.

The inventive gingival retraction material can also comprise one or more astringents (sometimes also referred to as haemostatic agent). Astringent(s) that may be useful in assisting haemostasis include, but are not limited to oxides, chloride or sulphate salts of ferrum (e.g. ferric sulfate, ferric subsulfate, ferric chloride), aluminium (e.g. potassium aluminum sulfate, aluminum ammonium sulfate, aluminum sulfate, aluminum chlorohydrate, aluminum acetate) and zinc, polyphenols, ellag acid, permanganates (e.g. potassium permanganate), potassioum ferrate (IV), silver nitrate and hydrogen peroxide, epinephrine and mixtures thereof. One preferred class of haemostatics include aluminum compounds.

The inventive gingival retraction material can also comprise one or more additives. Additives, which can be present in the composition, include colorants, pharmaceutical drugs, anti-microbial agents, anti-evaporation agents, rheology modifiers, flavoring agents, preserving agents, surfactants, pH buffering agent and mixtures and combinations thereof.

A typical inventive dental retraction composition may have the following formulation:
  liquid in an amount from about 15 wt.-% to about 30 wt.-%.
  a phyllosilicate e.g. a type 2:1 silicate mineral or a type 1:1 silicate material in an amount from about 50 wt.-% to about 70 wt.-%.
  an astringent in an amount from about 10 wt.-% to about 20 wt.-%.
  other additives in an amount up to about 10 wt.-%.

Another typical inventive dental retraction composition may have the following formulation:
- liquid in an amount from about 15 wt.-% to about 50 wt.-% or from about 16 wt.-% to about 40 wt.-% or from about 17 wt.-% to about 30 wt.-%.
- layer type 1:1 silicate mineral in an amount from about 1 wt.-% to about 34 wt.-% or from about 2 wt.-% to about 30 wt. % or from about 2.5 wt.-% to about 25 wt.-%.
- the layer type 2:1 silicate mineral in an amount from about 30 wt.-% to about 65 wt.-% or from about 31 wt.-% to about 64 wt.-% or from about 32 wt.-% to about 63 wt.-%.
- astringent in an amount from about 0.01 wt.-% to about 30 wt.-% or from about 5 wt.-% to about 20 wt.-% or from about 10 wt.-% to about 15 wt.-%.
- additives in an amount from about 0.0001 wt.-% to about 10 wt.-% or from about 1 wt.-% to about 7 wt.-% or from about 2 wt.-% to about 5 wt.-%.

In particular dental impression materials that may be used with the present invention are available under the designation Impregum™, Penta™, Permadyne™, Express Penta™, Imprint™, from 3M ESPE AG, Germany.

The dental impression material may be used for gingival retraction. Further the dental impression material used for gingival retraction may form part of a dental impression. For example the dental impression material may be injected into the gingival sulcus of a tooth to cause a gingival retraction, and another dental impression material used to take an impression of the tooth may merge with the dental impression material in the gingival sulcus. Thus the final impression may include an impression of the tooth and an impression of at least part of the gingival sulcus of the same tooth, and the impression material from both the teeth and the sulcus(es) may be removed at once.

In one embodiment the dental composition is adapted to physically widen the gingival sulcus. The dental composition may further have a storage modulus which is sufficient to maintain the gingival sulcus in a retracted position, for example for a period of time of between about 30 seconds and about 10 minutes, particularly for a period of time of between about 1 minutes to 5 minutes, preferably for about 2 minutes. The dental composition (impression material or gingival retraction material) is preferably characterized in that it has a storage modulus of at least about 2000 kPa.

In one embodiment the device of the invention comprises a cartridge having a chamber for holding the dental composition. The device is preferably adapted for comprising a piston, or may comprise a piston. The device is preferably adapted for dispensing the dental composition through the cannula. The cartridge may extend along a longitudinal axis, and the piston may be movable along the longitudinal axis for urging the dental composition towards the cannula. The chamber may, for example open into a nozzle to which the cannula can be adapted. Alternatively the chamber may open into the cannula. The cannula may be fixedly attached to the cartridge. For example, the cannula and the cartridge may be co-injection molded. In another embodiment the cannula and the cartridge are made from different plastic materials. For example the cartridge may be made of a more rigid plastic material than the cannula. Therefore the cartridge may provide sufficient stability for extruding the composition, and the cannula may be sufficiently soft to reduce the risk of injuries of the gingiva while in use.

In another embodiment the cannula extends along a longitudinal axis which is inclined relative to the longitudinal axis of the cartridge by an angle of between about 30 degrees and about 60 degrees, preferably by about 45 degrees. The cannula may also extend along a curve, and a central axis through the opening of the cannula may be inclined relative to the longitudinal axis of the cartridge by an angle of between about 30 degrees and about 60 degrees, preferably by about 45 degrees.

In another embodiment the cannula comprises a passageway between the opening with the first inner diameter P1 and an inlet with a second inner diameter P2, wherein P2 is between about 0.2 mm and 2.0 mm, in more particular P2 is between about 0.3 mm and 1.6 mm, and preferably P2 is about 1.2 mm. P2 is preferably greater than or equal to P1. Thus the passageway may taper towards the opening which may in dispensing certain dental compositions provide for a reduced extrusion force. Alternatively the passageway may be generally cylindrical which may facilitate manufacturing.

In another embodiment the convexly tapered outer surface of the free end may meet with the inner surface of the passageway at an angle of less than 90 degrees. It has been found that an angle below 90 degrees between the outer surface of the free end and the inner surface of the passageway may provide for a relatively low force required to insert the front of the free end into the entry of the gingival sulcus.

Particular embodiments may comprise the following configuration:

|    | Embodiment 1 [mm]      | Embodiment 2 [mm]      | Embodiment 3 (preferred) [mm] |
|----|------------------------|------------------------|-------------------------------|
| D1 | about 0.2 to about 1.0 | about 0.3 to about 0.7 | about 0.4                     |
| D2 | about 0.6 to about 1.5 | about 0.9 to about 1.4 | about 1.0                     |
| D3 | about 0.6 to about 2.5 | about 0.9 to about 1.9 | about 1.8                     |
| P1 | about 0.2 to about 1.0 | about 0.3 to about 0.8 | about 0.4                     |
| P2 | about 0.2 to about 2.0 | about 0.3 to about 1.6 | about 1.2                     |
| L1 | about 4.0 to about 18.0| about 6.0 to about 14.0| about 11.0                    |
| L2 | about 0.3 to about 2.0 | about 0.6 to about 1.5 | about 1.0                     |

In one particular embodiment of the invention the cannula comprises:
- a first outer diameter D1 of about 0.4 mm, and
- a second outer diameter D2 of about 1.0 mm;
- wherein first outer diameter D1 is located adjacent the front end of the free end, and the second outer diameter D2 is located at a distance L2 further to the rear from the first outer diameter D1; and
- wherein the distance L2 is about 1.0 mm; and
- wherein the first outer diameter D1 is formed by the opening, the opening therefore having a first inner diameter P1 which approximately corresponds to the outer diameter D1; and
- wherein the lateral outer surface of the free end convexly tapers from the second outer diameter D2 toward the first outer diameter D1, and wherein the convex taper in a direction from D2 toward D1 tapers based on a curve that approximates a radius R which is about 3.0 mm; and
- wherein the cannula further has a length L1 between the first outer diameter D1 and a third outer diameter D3, wherein the third outer diameter D3 is about 1.8 mm, and wherein the length L1 is about 11.0 mm; and wherein the device further comprises:
- a container for receiving the dental composition, the container being in fluid communication with the cannula;
- a piston movable in the container along an extrusion path for advancing the dental composition from the container toward the cannula,
- a catch extending laterally to the extrusion path and adapted to catch the device against movement in a direction parallel to the extrusion path, and a resilient adapter, wherein the resilient adapter is laterally resilient relative to the extrusion path; and wherein
the device further contains a dental composition which comprises:
   a liquid in an amount from about 15 wt.-% to about 30 wt.-%;
   a layer type 1:1 silicate mineral in an amount from about 1 wt. % to about 40 wt.-%;
   a layer type 2:1 silicate mineral in an amount from about 30 wt.-% to about 69 wt.-%;
   an astringent in an amount from about 0 to about 25 wt.-%; and
   additive(s) in an amount from about 0 to about 10 wt.-%; wt.-% with respect to the whole composition.

Such a particular embodiment was found to be of particular advantage for use in a gingival retraction treatment.

A fourth aspect of the invention is directed to a method of retracting the gingiva from a human tooth. The method comprises the steps of:
   providing a cannula having a free end with an opening for dispensing a dental composition;
   positioning the cannula within the entry of the gingival sulcus between the gingiva and the tooth;
   inserting the cannula into the entry of the gingival sulcus and thereby laterally displacing the gingiva from the tooth; and
   providing a dental composition from the opening into the gingival sulcus.

The method of the invention may provide for filling the gingival sulcus with the dental composition from the bottom of the gingival sulcus towards the top, or from the top down to the bottom. The dental composition therefore preferably continuously fills the gingival sulcus between the bottom and top, and preferably becomes visible at the entry of the sulcus. Thus, the gingival sulcus may be filled with relatively few voids, air bubbles, or pockets. Further such a method may provide for keeping areas adjacent the entry of the gingival sulcus preferably substantially free of dental composition. Therefore the entry of the gingival sulcus may remain visible, which may help a dentist to reliably recognize which parts of the gingival sulcus have been filled sufficiently.

It has also been found that the method of the invention may provide for filling the dental composition relatively deeply into the gingival sulcus, without substantially affecting the epithelial attachment. Therefore relative to known gingival retraction methods a more reliable but at the same time more acceptable gingival retraction may be achieved with the method of the invention. Consequently a subsequent impression may be taken at an acceptable quality. The current practice of repeated impressions and gingival retractions may therefore be avoided. Thus the present invention may also help to save waste and cost in a dental practice.

In an embodiment of the invention the method comprises observing an area of the gingiva (for example an area adjacent the entry of the gingival sulcus) for changes in color, and depending on a color change controlling the flow of the dental composition. It has been found that the gingiva tends to change in color, for example turn pale, when it is retracted from the tooth. Therefore a user may stop injecting dental composition as a certain color change occurs. Thereby the gingival retraction method may be relatively gentle for a patient.

In another embodiment the method of the invention further comprises the step of moving the cannula of the invention along at least a part of the circumference of the tooth. Preferably the opening of the cannula is inserted in the gingival sulcus, and preferably further dental composition is extruded while the cannula is moved along at least a part of the circumference of the tooth.

In another embodiment the dental composition is a dental impression material or a gingival retraction material, and wherein the dental impression material is as specified above.

In one embodiment the method comprises the use of an applicator that reduces the manual force applied to the applicator for extrusion of the dental composition to an extrusion force applied by a plunger of the applicator to the dental composition, wherein the ratio of the extrusion force relative to the hand force is about 1:3, about 1:7, about 1:8, about 1:10, or less. The extrusion force for extruding a gingival retraction material may for example be between about 50 N and 300 N, particularly about 100 N. By use of an applier that extrusion force may be converted to hand force down to about 25 N. Therefore a relatively convenient handling may be provided. The extrusion force for extruding an impression material may for example be between about 10 N and 150 N, particularly about 30 N. By use of an applier that extrusion force may be converted to hand force down to about 10 N.

A fifth aspect of the invention relates to a kit of parts which comprises a device for dispensing a dental composition, a cannula having a free end with an opening for dispensing a dental composition and instructions that are adapted to instruct a user to perform a method comprising the steps of:
   positioning the cannula with the opening to the entry of the gingival sulcus which is formed between the gingiva and the tooth;
   moving the cannula toward the gingival sulcus to insert the opening into the entry of the gingival sulcus and thereby laterally displacing the gingiva from the tooth; and
   extruding a dental composition from the opening into the gingival sulcus.

DETAILED DESCRIPTION OF THE FIGURES

In the following the invention is explained by way of example only, introduced by a procedural background about tooth restoration.

Figure 1:
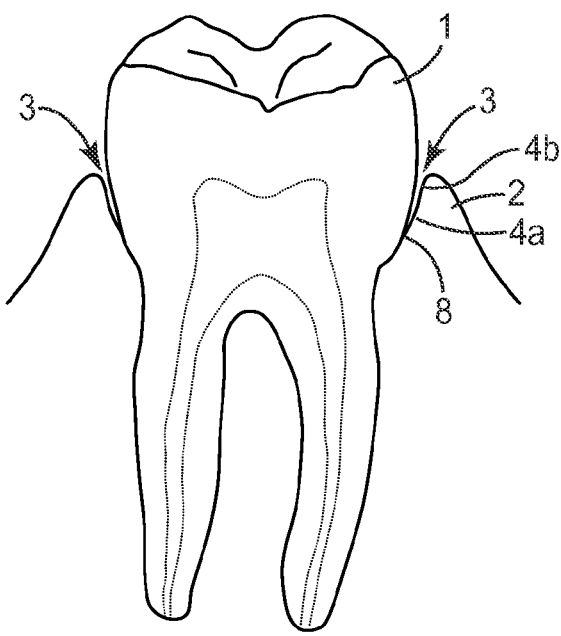
FIG. 1 is a cross-sectional view of a natural tooth and part of a gingiva.

FIG. 1 illustrates a cross-section of a natural human tooth 1 in its typical position in a patient's mouth. The tooth 1 is surrounded by the gingiva 2. As indicated the gingiva 2 typically abuts the tooth 1 in at least a lower area 4a, and typically extends slightly away from the tooth 1 in an upper area 4b. The borderline between the lower area 4a and the upper area 4b typically is formed by the so-called epithelial attachment 8. The epithelial attachment 8 further typically characterizes a zone at which the gingiva and the tooth are adhered. The upper area 4b between the gingiva and the tooth is the gingival sulcus 3. The gingival sulcus 3 may form a crevice between the tooth 1 and the gingival 2. The gingival sulcus in a healthy gingiva may have about a depth of about up to 2 mm, and a width of 0.2 mm or less. Healthy gingiva above the epithelial attachment 8 may also abut the tooth.

Figure 2:
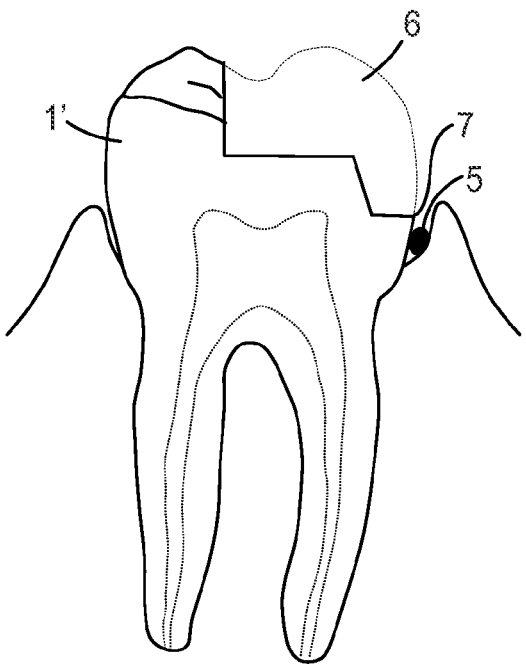
FIG. 2 is a cross-sectional view of a natural tooth prepared for restoration with the gingiva retracted by a retraction cord.

FIG. 2 shows a natural tooth 1' which has been prepared for restoration. The example illustrates a preparation for a partial crown for which reason only a section 6 of the tooth periphery is removed. Typically a preparation of a tooth includes taking away sufficient tooth structure to remove pathological tissue (for example carious tooth tissue), and further providing space for a restoration to be attached on the prepared tooth.

The preparation shown in the Figure extends beneath the level of the gingiva so as to hide the transition between the natural tooth 1 and the later dental restoration, and in particular the adhesive or other material used to attach the two parts, behind the gingiva. Thereby the aesthetics of the finished restored tooth in a patient's mouth can be optimized. In the example a retraction cord 5 is placed into the gingival sulcus and displaces the gingiva from the tooth V. Thereby the preparation margin 7 is made accessible so that it can be replicated in an impression that may in a separate step be made from the tooth.

Figure 3:
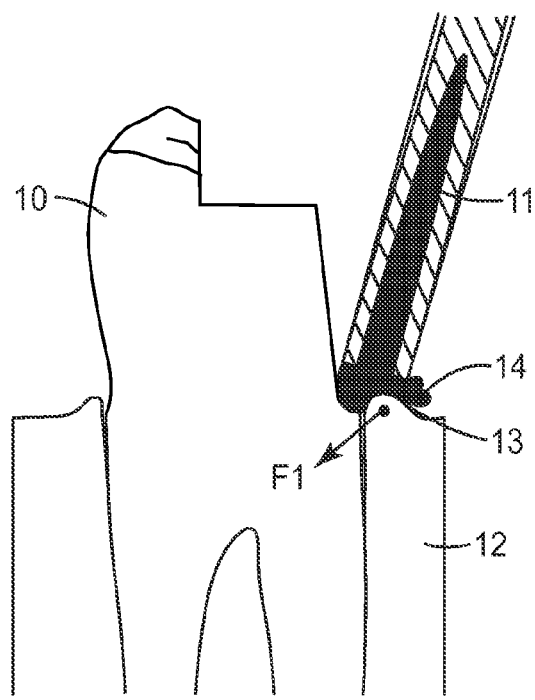
FIGS. 3, 3A are views of a natural tooth prepared for restoration and a cannula according to background art.
Figure 3A:
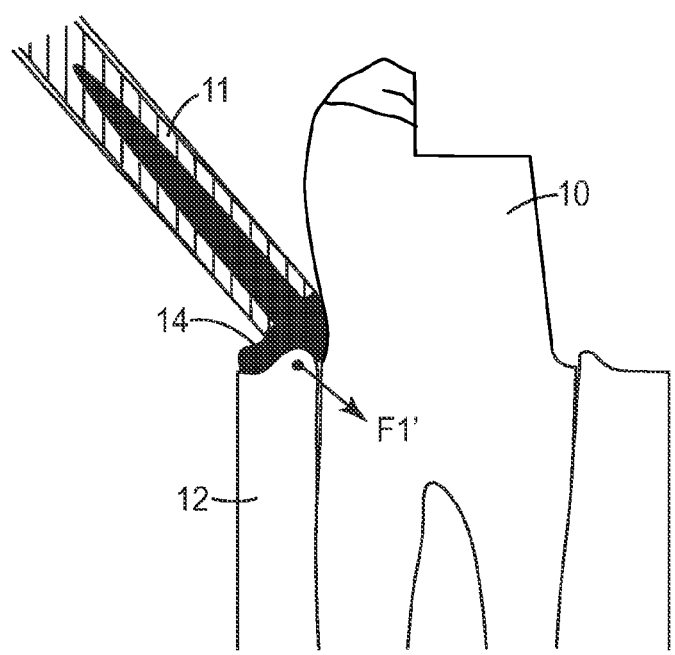

FIGS. 3 and 3A show a known device for gingival retraction by use of a known dental retraction paste 14. In the example a tooth 10 is prepared to receive a partial crown, for example a crown that replaces some of the top and the lateral sides of the tooth 10. FIG. 3 illustrates a situation in which paste is dispensed from an opening 13 toward the gingival sulcus adjacent the prepared lateral side of the tooth 10, and FIG. 3A shows a similar situation at another lateral side of the tooth 10 which is not prepared. A known cannula 11 for dispensing the typically very high-viscosity known dental retraction paste is positioned at the gingival tissue 12 above the gingival sulcus 13, and paste 14 is dispensed towards the gingival sulcus 13. The paste is pushed toward the gingival sulcus 13 by pressurizing the paste 14 at the entry of the gingival sulcus, for example by further dispensing paste and/or pushing the cannula 11 toward the gingival sulcus. Typically the paste is pressurized in an area outside the gingival sulcus so as to force the paste from outside into the gingival sulcus. Therefore such a procedure also typically requires a relatively high-viscosity paste having stability sufficient to build up pressure in the paste to cause the paste to flow into the gingival sulcus. However, as indicated the paste may tend to deform or flow under pressure and to spread over parts of the gingival sulcus and surrounding tissue. Further, for example depending on the particular geometrical situation of the tooth and gingiva, and/or depending on the user, pushing the paste toward the gingival sulcus may in some instances urge the gingiva toward the tooth as indicated by the resulting force F1. This may for example force the entry of the gingival sulcus to close so that paste is hindered from penetrating into the gingival sulcus. It has also been found that such known procedures in some instances can fail to force paste sufficiently deep into the gingival sulcus so that an impression taken from the respective tooth may not represent the preparation margin or other features of the prepared tooth properly. Particularly in a situation in which the gingival sulcus is located adjacent not prepared or natural areas of the tooth, for example as shown in FIG. 3A, the space for placing the cannula toward the gingival sulcus may be limited relative to a situation shown in FIG. 3. Thus, in a situation as shown in FIG. 3A, to direct the opening of the cannula toward the entry of the gingival sulcus a user may tend to angle the cannula less steep relative to a situation shown in FIG. 3, and thereby cause an even increased force urging the gingiva toward the tooth relative the situation shown in FIG. 3.

Figure 4:
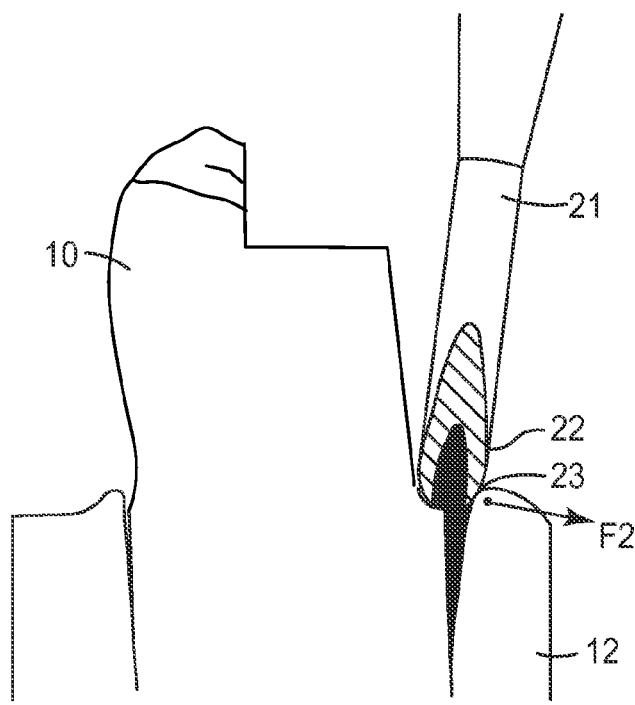
FIGS. 4, 4A are views of a natural tooth prepared for restoration and a cannula according to an embodiment of the invention.
Figure 4A:
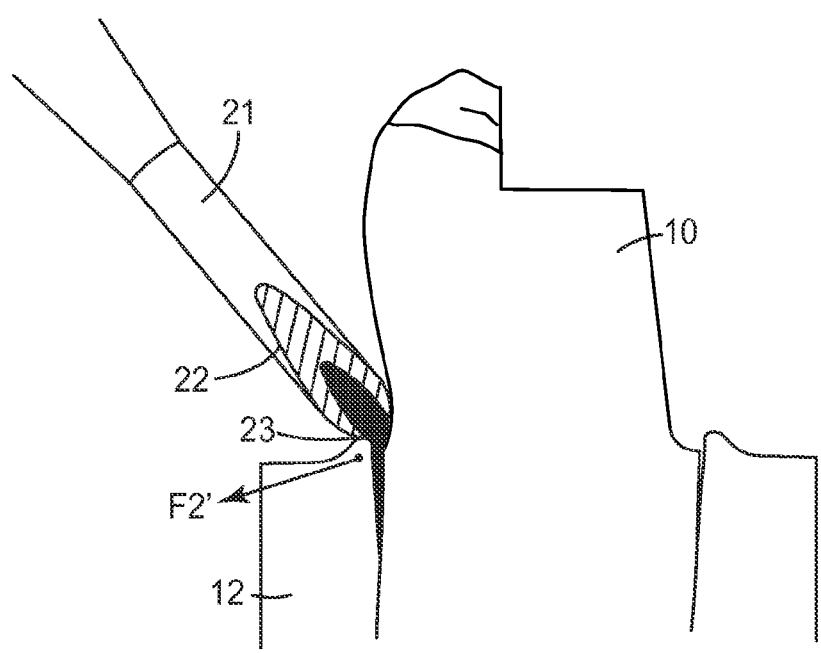

FIGS. 4 and 4A show, in contrast to the situation in FIGS. 3 and 3A, the cannula 21 of the invention. FIG. 4 illustrates a situation at the gingival sulcus adjacent the prepared lateral side, and FIG. 4A illustrates a similar situation at another lateral side of the tooth 10 which is not prepared. The cannula 21 has a tapered free end 22 with an opening 23 for dispensing a dental composition. The free end 22 of the cannula 21, because of the taper, has a relatively small diameter at its front end, or front most end, and thus can be placed between the gingiva 12 and the prepared tooth 10. On the other hand because the taper is convex, the free end already has a relatively large diameter adjacent the opening 23. This may allow for displacing the gingiva 12 from the tooth 10 with only slightly inserting the free end 22 between the gingiva 12 and the prepared tooth 10. The free end 22 of the cannula 21 is placed between the gingiva 12 and the prepared tooth 10 so that the gingiva 12 is slightly displaced laterally, away from the tooth 10. This is indicated by a resulting lateral force F2. Because of the shape of the free end 22 of the cannula 21 even in a situation in a situation in which the gingival sulcus is located adjacent natural areas of the tooth (FIG. 4A) the gingiva 12 may be exposed to a resulting lateral force F2 oriented to cause the gingival sulcus to open rather than to close as indicated in FIGS. 3 and 3A. The opening 23 is located in the opened gingival sulcus so that dental composition dispensed from the cannula 21 flows into the gingival sulcus. In fact, it has been found that a shallow insertion of the cannula and therefore moderate mechanical opening of the gingival sulcus by the cannula is sufficient to achieve a relatively good penetration of the dental composition in the gingival sulcus. This is because initial amounts of dental composition injected into the gingival sulcus tend to cause further opening of the gingival sulcus, which again facilitates further injection of dental composition. Thus the invention may allow for properly filling the gingival sulcus with the dental composition, and thereby may provide for a reliable gingival refraction, and proper impressioning of the preparation margin. Because the dental composition is injected into the opened gingival sulcus the gingiva preferably also remain generally uncovered from dental composition. Therefore areas around the entry of the gingival sulcus preferably remain visible, for example to a dentist. In particular a dentist may observe the color of the gingiva, which tends to turn pale when refracted from the tooth. It has been found that therefore the amount of dental composition dispensed in the gingival sulcus can be relatively well controlled. Thereby the pressure of the dental composition within the gingival sulcus may be kept below limits that would cause the epithelial attachment to be affected. As a result, the risk of detaching the epithelial attachment may be reduced. This is advantageous because tearing the epithelial attachment from the tooth can cause diseases of the gingiva and/or the jaw due to possible penetration of bacteria deeply into the tissue between the tooth and the gingiva.

Furthermore, it has been found that in contrast to known procedures, a lower viscosity dental composition may be used. This is enabled by the invention, for example, because the dental composition is injected within the slightly opened gingival sulcus, rather than being pushed in from outside the gingival sulcus. Therefore in one embodiment the preferred dental composition has a relatively low viscosity. A lower viscosity dental composition typically allows for example dispensation at lower extrusion forces, which may be more convenient for a user and the patient.

Figure 5:
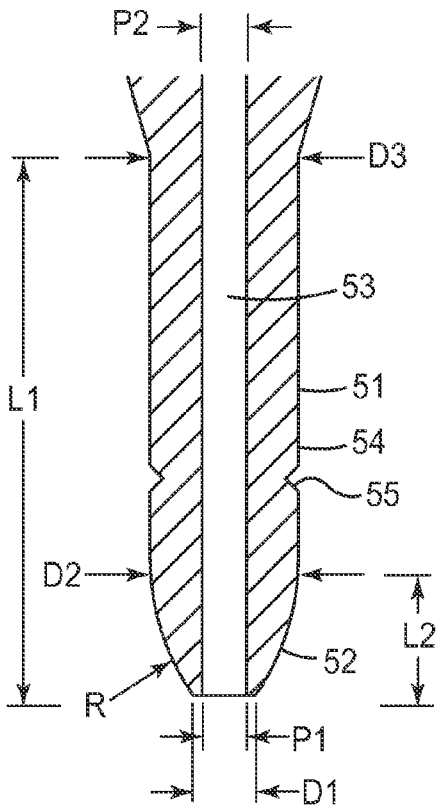
FIG. 5 is a cross-sectional view of a cannula according to an embodiment of the invention.

FIG. 5 shows a cannula 51 according to an embodiment of the invention. The cannula 51 has a shaft portion 54 and a front or free end 52. The cannula 51 further comprises a passageway 53 having an inner front diameter P1 and an inner rear diameter P2. The passageway 53 may be cylindrical. In this case the inner front and rear diameters P1, P2 are generally equal. In another embodiment the inner front and rear diameters P1, P2 may be different. The passageway 53 may taper from the inner rear diameter P2 toward the inner front diameter P1, in which case P2 is greater than P1. This may for example provide for relatively lower forces required to move a dental composition through the cannula, may even also enable the use of high viscosity compositions although in some instances low viscosity material may be preferred.

Test:

The extrusion force for extruding a dental refraction composition through cannula having a tapered passageway was compared to the extrusion force for extruding the same material through a cannula having a non-tapered passageway (one having a generally uniform dimension over its length).

The cannula with the tapered passageway had an inner front diameter P1 of about 0.4 mm. The cannula and the passageway had a length of about 7.6 mm. An inner rear diameter P2 of the cannula was provided opposite of the inner front diameter. The taper was about 3 degrees measured in a plane along about the center of the passageway between opposing side walls of the passageway.

The cannula with the non-tapered passageway had an inner front diameter P1 of about 0.4 mm. The cannula and the passageway had a length of about 7.6 mm. The passageway had a diameter of about 0.4 mm over the entire length of the cannula.

The composition used for the test corresponded to a composition having the following formulation:
- liquid in an amount from about 15 wt.-% to about 50 wt.-% or from about 16 wt.-% to about 40 wt.-% or from about 17 wt.-% to about 30 wt.-%.
- layer type 1:1 silicate mineral in an amount from about 1 wt.-% to about 34 wt.-% or from about 2 wt.-% to about 30 wt. % or from about 2.5 wt.-% to about 25 wt.-%.
- the layer type 2:1 silicate mineral in an amount from about 30 wt.-% to about 65 wt.-% or from about 31 wt.-% to about 64 wt.-% or from about 32 wt.-% to about 63 wt.-%.
- astringent in an amount from about 0.01 wt.-% to about 30 wt.-% or from about 5 wt.-% to about 20 wt.-% or from about 10 wt.-% to about 15 wt.-%.
- additives in an amount from about 0.0001 wt.-% to about 10 wt.-% or from about 1 wt.-% to about 7 wt.-% or from about 2 wt.-% to about 5 wt.-%.

The Extrusion Force was Measured as Follows:

The extrusion force was measured using as testing device a Zwick Z020 machine (Zwick Roell Comp.). The testing device was equipped with a holder for a device for dispensing dental composition from a reservoir through a cannula and a small stamp to press against the piston inserted in the device and sealing the reservoir. The dimensions of the stamp corresponded to those used in commercially available single container dispensers (commercially available e.g. from 3M ESPE Comp.; order code 5706 SD). The feeding speed was set to 1.0 mm/s. The force was measured after the initial yield point was overcome (about 6-9 mm from starting point). The extrusion force was determined as an average value out of six individual measurements.

Result:

The extrusion force measured on the nozzle having the tapered passageway was about 135 N, and the extrusion force measured on the nozzle having the non-tapered passageway was about 190 N.

The cannula 51 further has a first outer front diameter D1. In the example shown the first outer front diameter D1 is greater than the inner front diameter P1. However in other embodiments the outer front diameter D1 may be the same or approximately the same as the inner front diameter P1. The outer front diameter D1 is preferably measured adjacent the inner front diameter P1. The cannula 51 further has a second outer front diameter D2 and an outer rear diameter D3. Preferably the inner front diameter P1 and/or the outer front diameters D1 form a front end of the free end 52. The free end 52 thus preferably extends between the first and second outer front diameters D1 and D2, or between the inner front diameters P1 and the outer front diameter D2. The shaft portion 54 of the cannula 51 may extend adjacent the free end 52 between the second outer front diameter D2 and the outer rear diameter D3. D2 and D3 may be generally equal, so that the shaft portion 54 is generally cylindrical. Alternatively D2 and D3 may be different, so that the shaft portion 54 is generally conical. For example D3 may be greater than D2, so that the shaft portion 54 tapers from D3 toward D2.

The cannula 51 also has a minimum overall length L1, and the free end 52 has a length L2 with the convex taper tapering along a curve that has an approximate radius R. The dimensions D2, D3, P1, P2, L1, L2 and R may be in within the ranges specified above. P1 and D1 may have equal diameters, however, D1 may be greater than P1 by between 0.05 to 1 mm, in particular by between 0.1 and 0.4 mm. Combinations of the dimensions specified above are possible as appropriate.

A preferred embodiment of the cannula 51 may have a passageway with an inner rear diameter P2 of about 1.15, and an inner front diameter P1 of about 0.4 mm, with the length of the passageway between the inner rear and front diameters P2, P1 being about 10.9 mm. The length of the passageway between inner rear and front diameters P2, P1 may for example correspond to the length L2. Preferably the passageway between the inner front and rear diameters P2, P1 tapers linearly or substantially linearly from the rear inner diameter P2 toward the front inner diameter P1. A cannula according to this preferred embodiment may further have a free end having a length L2 of about 1.03 mm, an outer front diameter D1 which corresponds generally to the inner front diameter P1, and an outer rear diameter of about 1.93 mm. The Radius R of this embodiment is preferably about 2.76 mm. It has been found that this embodiment facilitates supplying a gingival retraction material into a patient's gingival sulcus.

The cannula 51 in the example also has a marking 55 for reference with regard to a certain penetration depth of the cannula in the gingival sulcus. The marking 55 is formed as a circumferential notch. However, other embodiments are possible like transitions between colors or surface structures, rims, or lines, and combinations thereof, for example. The marking may help to reduce the risk of injuries of the gingival tissue, and/or help to provide a reliable gingival retraction procedure.

Figure 6:
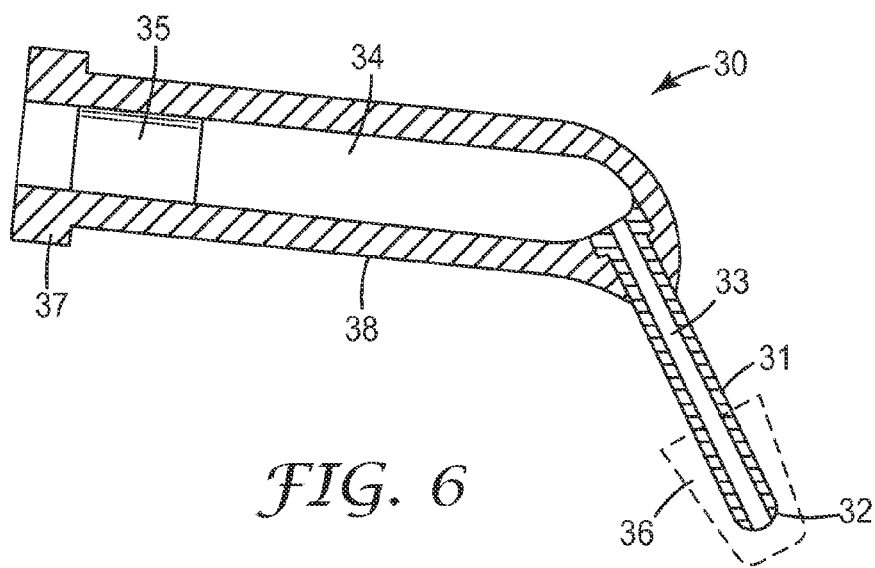
FIG. 6 is a cross-sectional view of a device according to an embodiment of the invention.

FIG. 6 shows an embodiment of a device 30 according to the invention. The device 30 has a cannula 31 with a convex tapered free end 32. The device 30 further has a reservoir 34 for holding a dental composition. A piston 35 closes the reservoir and is displaceable therein for extrusion of the dental composition from the reservoir 34. The reservoir 34 opens into a passageway 33 in the cannula 31. A removable cap 36 (indicated by dashed lines) may be used to close the passageway 33 until the device 30 is used. Further the cannula 31 may be closed with a plug (not shown). The plug may for example remove automatically when gingival retraction material is dispensed from the device 30. Preferably such a self-opening plug is formed of a material which can be applied to the same location the dental composition is applied to substantially without causing any inacceptable adverse impact. Such a plug may for example be formed of a wax or hardened dental composition. The device 30 may be used with an applicator device as available under the designation "5706 SD Capsule Dispenser" from 3M ESPE, Germany. Therefore the device 30 has a rim 37 which may be used for engaging the device 30 in the dispenser. The rim 37 may have a notch or flat to lock the device against unintentional rotation during use. Such anti-twist protection may also be otherwise achieved, for example by clamping the device, or by any other positive or frictional fit between the device and the applicator device.

Preferably the cannula 31 and the capsule body 38 are molded from different plastic materials. This allows, for example for selecting a relatively soft plastic material for the cannula 31 so that it can be conveniently used in direct contact with relatively sensitive tissue in a patent's mouth. On the other hand this allows for molding the capsule body 38 from a relatively rigid material which provides sufficient mechanical strength that may be required during extrusion of the dental composition from the device. The cannula 31 and the capsule body 38 may also be molded from different plastic materials. The cannula 31 may be integrally molded with the capsule body 38. This may for example be achieved by injecting a first plastic material into a mold at an end forming the cannula, and generally simultaneously injecting a second plastic material into the mold at an end forming the body. The flow rate of the individual plastic materials may be controlled so that the plastic materials join in an area where the cannula 31 merges with the capsule body 38. Another way to mold the device 30 from two plastic materials includes first molding the cannula 31 and subsequently molding the capsule body 38 onto the pre-molded cannula, or vice versa.

Preferred plastic materials for the cannula 31 are: polyethylene, polypropylene, Styrene-butadiene-styrene block copolymer, Styrene-butadiene-methacrylate block copolymer, thermoplastic polyurethane. The cannula may however further be made of metal, for example made of steel. This is enabled due to the shape of the cannula according to the invention, although a dentist would typically prefer soft materials for contacting sensitive tissue like the gingival sulcus. Preferred plastic material for the capsule body 38 are: polyamide, polyoxymethylene, polypropylene, polycarbonate.

Figure 7:
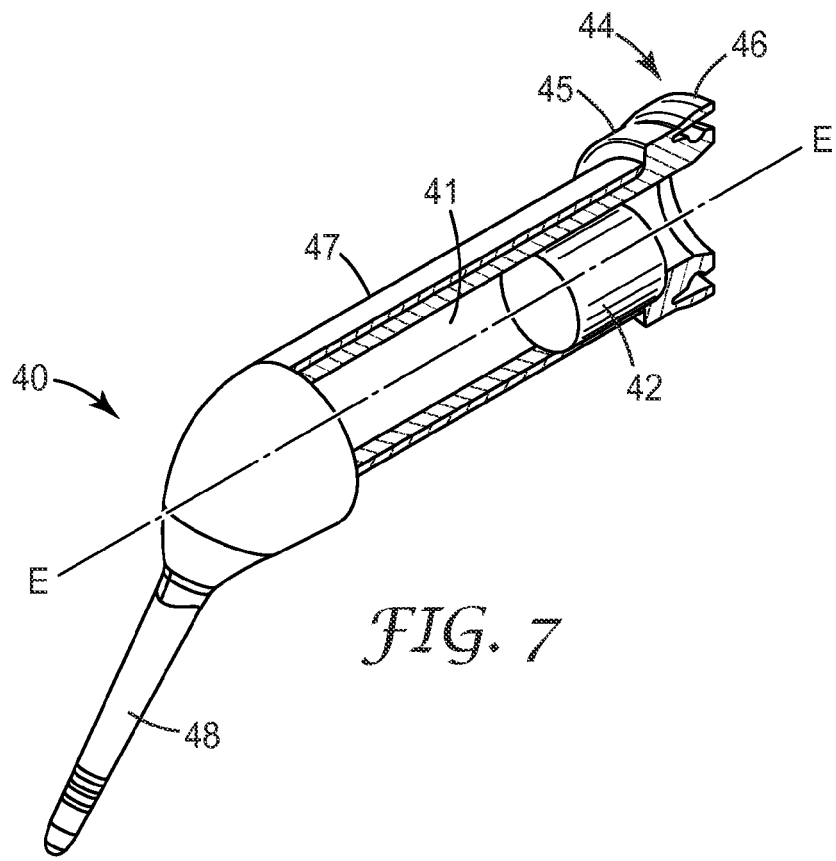
FIG. 7 is a cross-sectional view of a further device according to an embodiment of the invention.

FIG. 7 is a partial cross-sectional view of a device 40 according to another embodiment of the invention. The device has a chamber 41 which may receive the gingival retraction material. A piston 42 for advancing the gingival retraction material is received in the chamber. The device 40 has a dispensing end 43 from which the dental substance may be dispensed and a back end 44 which is configured to use the device 40 with an applicator. An applicator as it may be used with the present invention is for example available from 3M ESPE AG, Germany under the designation Capsule Dispenser. The back end 44 of the device 40 comprises a catch 45 and a resilient adapter 46. The catch 45 and the resilient adaptor 46 allow the device 40 to be retained in the applicator. The applicator may facilitate dispensing of the dental substance from the dispensing end 43.

The device 40 has further a container 47 and may have a cannula 48. The container 47 in the illustrated example extends generally linearly along an axis E-E and the cannula 48 extends generally linearly in an angle therefrom. This configuration may for example facilitate reaching certain places in a patients' mouth with the cannula during a dental treatment. The skilled person may however appreciate other configurations, for example configurations in which the cannula and the container are co-aligned or parallel with one another. Further the container 47 may extend along a curve, for example a circular or generally circular curve. In this example the cannula may be co-aligned with the curve the container extends along. Thus a configuration is provided which may be likewise suitable to reach certain locations in a patient's mouth.

Figure 8:
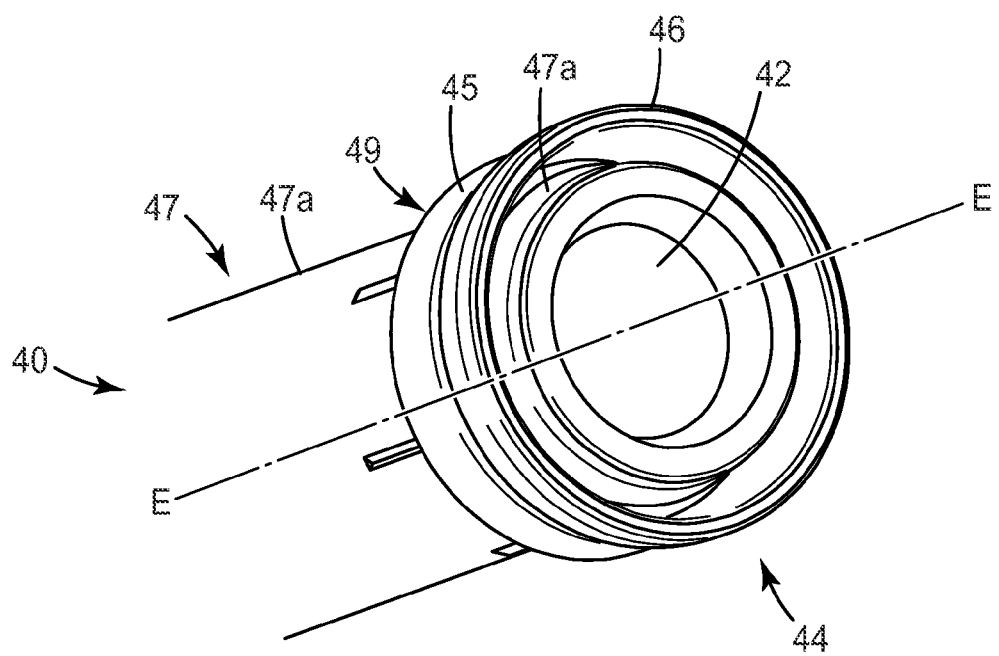
FIG. 8 is a perspective detail view of the embodiment shown in FIG. 7.

FIG. 8 shows in detail the back end 44 of the device 40. The catch 45 is preferably adapted to prevent movement due to forces in a direction of the axis E-E. In particular the catch 45 may be adapted to retain the device 40 against forces that are exerted to the piston 42 for advancing of the material stored in the device. The catch 45 in the example is arranged as an annular rim around a section of the container 47. In particular the catch 45 may be a generally solid rim which is preferably formed in one piece with the container. Other configurations are possible. For example the annular rim may be notched. Further, instead of a rim, at least one individual retention member that protrudes from the outer surface of the container 47 may be used as a catch. In another embodiment the catch may be formed by a rim which is supported by webs that connect the outer surface of the container and a rear face (facing toward the back end of the device) of the rim. The catch may in any embodiment have a front face 49 which extends generally transverse or radially away from the outer surface of the container 47. Therefore the catch may form a step on the container 47. This may help securely retaining the device in the applicator. The back end 44 further has a resilient adapter 46. In the example the resilient adapter 46 protrudes from the rear face of the rim backwards (toward the back end 44). The resilient adapter 46 is generally ring shaped. Preferably the resilient adapter is formed in one piece with the catch. However the resilient adapter may also be separately formed, for example formed from another material than the catch. The resilient adapter 46 may be formed, as shown, as a relatively thin ring which is spaced from the outer surface 47a of the container. The resilient adapter 46 therefore provides certain elasticity relative to the catch 45. Thus the resilient adapter 46 preferably is resiliently deformable laterally to the axis E-E. The resilient adapter 46 may be used for laterally positioning the capsule in the applicator.

Other configurations for the resilient adapter are possible. For example the container may be provided with at least one radially protruding annular flash or rib.

EXAMPLES

Figure 9:
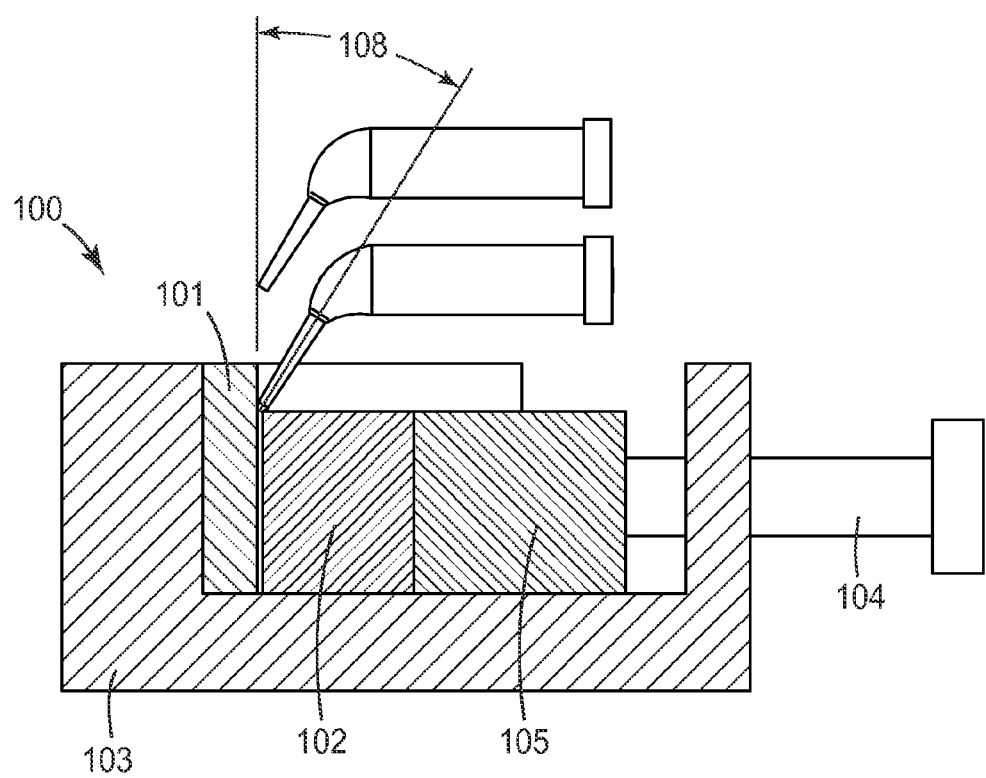
FIG. 9 is a cross-sectional view of a test device for evaluating the potential penetration depth of a composition into a gingival sulcus.

FIG. 9 shows a test device 100 for evaluating the efficiency of a gingival retraction. The device basically has two jaws between which a dental composition can be forced, for example by a device as described herein for dispensing a dental composition. The jaws can be separated to assess to what depth the dental composition has penetrated between the jaws. In particular the test device has a "hard jaw" 101 that simulates a tooth, and a "soft jaw" 102 that simulates the gingiva. The hard jaw 101 is made of a relatively unelastic or hard material. In this example the hard jaw 101 is made of polytetrafluoroethylene (PTFE). PTFE generally provides compositions used in the test to be removed from the jaw relatively easily so that it facilitates cleaning of the test device. However any other suitable plastic or metal may be used. The soft jaw 102 in the example is made from gingival mask material Gi-Mask by Coltène/Whaledent AG, Switzerland. The soft jaw 102 therefore has a material characteristic that resembles that of natural gingiva. The hard and soft jaws 101, 102 each have a generally flat test surface that are arranged opposite and generally parallel to one another. The jaws 101, 102 and are mounted in a parallel vice 103 so that the soft jaw 102 is adjustable relative to the hard jaw 101 by a jackscrew 104. The jackscrew is adapted to move an adjustable block 105 at which the soft jaw 102 is fixed. The test surfaces of the jaws 101, 102 can thus be adjusted at different distances relative to one another, or with the test surfaces touching or pressing on each other.

To resemble the geometric situation between natural gingiva adjacent a natural tooth, the hard jaw 101 protrudes over the soft jaw 102 in a direction laterally of the test surfaces so that a step is formed by the jaws 101, 102 when moved together.

Example 1.1

The test device was adjusted with the test surfaces of the jaws 101, 102 spaced from each other at about 0.2 mm. The crevice of 0.2 mm between the jaws 101, 102 was selected in accordance to the biological width of a natural gingival sulcus crevice as mentioned in the references "Laufer, Ben-Zion, DMD, MSD; Baharav, Haim, DMD, MSc; Cardash, Harold S, BDS, LDS, RCS (Eng): The Linear Accuracy of Impressions and Stone Dies as Affected by the Thickness of the Impression Margin", and "Laufer, Ben-Zion, DMD, MSD; Baharav, Haim, DMD, MSc; Ganor, Yehuda, DMD; Cardash, Harold S., BDS: The effect of marginal thickness on the distortion of different impression materials".

A device having a cannula according to the invention was filled with a dental composition as available under the designation Expasyl™, form the company Produits Dentaires Pierre Rolland, France, further referred to as "Expasyl". The device generally corresponded to a device as shown in FIG. 6. The cannula has the dimensions as specified in Table 1:

TABLE 1

|  | D2 | D3 | P1 = D1 | P2 | L1 | L2 | R |
|---|---|---|---|---|---|---|---|
| Cannula of Examples 1.1, 1.2, 1.3 | 1.3 | 1.3 | 0.6 | 0.6 | 10 | 1 | 0.7 |

(all dimensions in mm; D1, D2, D3, P1, P2, L1, L2 and R as indicated in FIG. 5)

The cannula was placed with its free end to the crevice between the jaws 101, 102. The cannula thereby was oriented at about 45° relative to the test surfaces (indicated by reference number 108). The Expasyl was extruded by moving the piston of the device at a speed of about 2 mm per second. The piston used for extruding the Expasyl in Example 1.1 had a diameter of about 4.1 mm, so that the extrusion rate was about 26.4 mm$^3$ per second.

Examples 1.2 and 1.3

Example 1.1 was repeated using the same device and cannula, but in Example 1.2 with the jaws 101, 102 spaced at a distance of about 0.3 mm, and in Example 1.3 spaced at a distance of about 0.4 mm.

Example 2.1, 2.2, 2.3

Examples 2.1, 2.2 and 2.3 correspond to the Examples 1.1, 1.2 and 1.3, but a different cannula according to the invention was used. The dimensions of the cannula used in Examples 2.1, 2.2 and 2.3 are given in Table 2.

TABLE 2

|  | D2 | D3 | P1 = D1 | P2 | L1 | L2 | R |
|---|---|---|---|---|---|---|---|
| Cannula of Examples 2.1, 2.2, 2.3 | 1.1 | 1.7 | 0.4 | 1.0 | 10 | 0.45 | 0.65 |

(all dimensions in mm; D1, D2, D3, P1, P2, L1, L2 and R as indicated in FIG. 5)

Comparative Examples 3.1, 3.2, 3.3

Examples 1.1, 1.2, and 1.3 have been repeated with a known device and a known cannula. The cannula used in Comparative Examples 3.1, 3.2 and 3.3 had dimensions as specified in Table 3. The Expasyl in Comparative Examples 3.1, 3.2 and 3.3 was extruded by moving the piston of a known device at a speed of about 2 mm per second. The piston used for extruding the Expasyl in Comparative Examples 3.1, 3.2 and 3.3 had a diameter of about 4.5 mm, so that the extrusion rate was about 31.8 mm$^3$ per second.

TABLE 3

|  | D1 = D2 = D3 | P1 = P2 | L1 | L2 | R |
|---|---|---|---|---|---|
| Cannula of Comparative Examples 3.1, 3.2, 3.3 | 1.6 | 1.2 | 20 | n/a | n/a |

(all dimensions in mm; D1, D2, D3, P1, P2, L1, L2 and R as indicated in FIG. 5)

Results of the Examples and Comparative Examples

Figure 10:
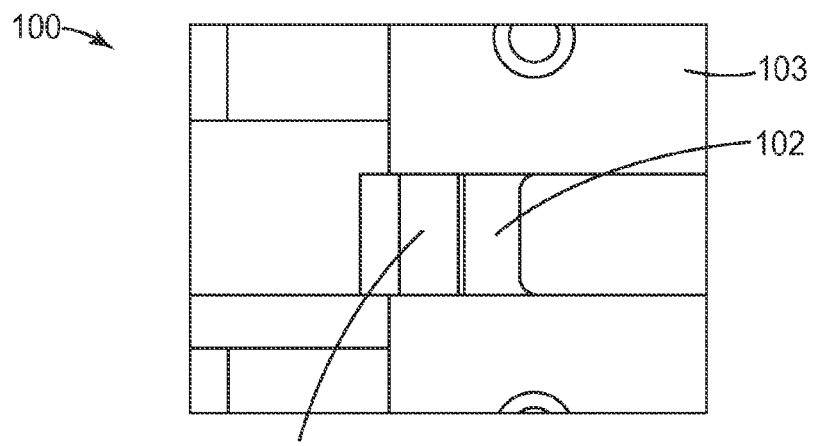
FIGS. 10, 11, 12 are perspective views of the test device illustrated in FIG. 9.
Figure 11:
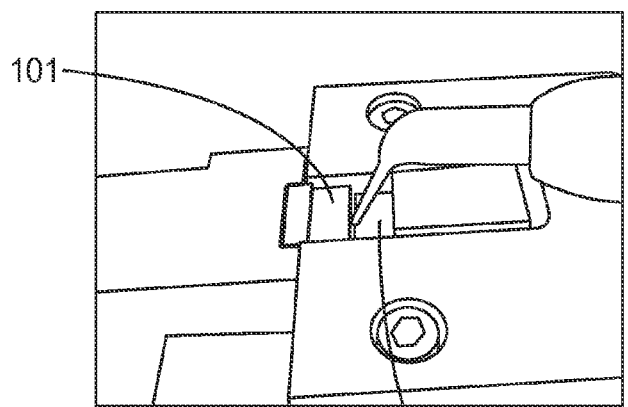
Figure 12:
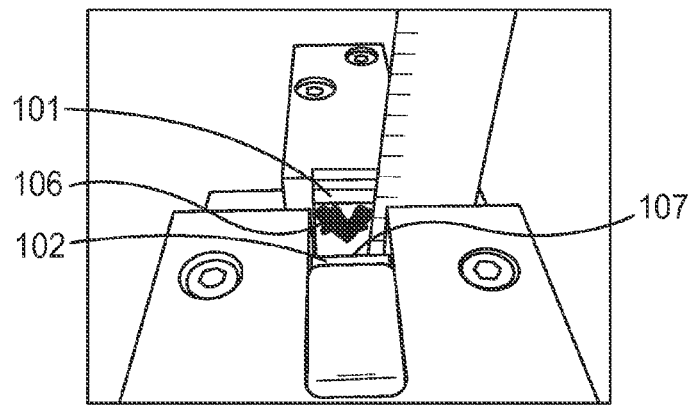

FIGS. 10 to 12 show perspective views of the test device 100 used for the Examples and Comparative Examples. FIG. 10 shows a top view of the device 100. The hard and soft jaws are indicated by reference numbers 101, 102 respectively. Further a portion of the parallel vice 103 is shown. FIG. 11 shows the test device 100 with the cannula placed to the crevice between the jaws 101, 102, and FIG. 12 shows the test device 100 with the jaws 101, 102 spaced away from another to allowing the penetration depth to be assessed. The dental composition penetrated between the jaws 101, 102 is indicated by reference 106. The depth to which the dental composition has penetrated was measured for each of the Examples 1.1-1.3, 2.1-2.3, and for Comparative Examples 3.1-3.3 using a steal ruler. The depth thereby was evaluated from the distance from the upper corner 107 of the jaw 102 to the lowest point of the dental composition adhering to one of the jaws. The test results are given in Table 4.

TABLE 4

|  | Example 1.1 >crevice 0.2 mm< Penetration depth [mm] | Example 1.2 >crevice 0.3 mm< Penetration depth [mm] | Example 1.2 >crevice 0.4 mm< Penetration depth [mm] |
|---|---|---|---|
| Cannula acc. to Examples 1.1-1.3 | 2 | 3 | 3 |
| Cannula acc. to Examples 2.1-2.3 | 3 | 3 | 3 |
| Cannula acc. to Comparative Examples 3.1-3.3 (known cannula) | 0 | 0 | 3 |

Examples 1.1-1.3, Examples 2.1-2.3 and Comparative Examples 3.1-3.3 have been repeated to confirm the results compiled in Table 4. The results of the confirmation tests are given in Table 5:

TABLE 5

|  | Example 1.1 >crevice 0.2 mm< Penetration depth [mm] | Example 1.2 >crevice 0.3 mm< Penetration depth [mm] | Example 1.2 >crevice 0.4 mm< Penetration depth [mm] |
|---|---|---|---|
| Cannula acc. to Examples 1.1-1.3 | 1.8 | 3 | 3 |
| Cannula acc. to Examples 2.1-2.3 | 3 | 3 | 3 |
| Cannula acc. to Comparative Examples 3.1-3.3 (known cannula) | 0 | 0 | 3 |

In the Examples a relatively deep penetration of dental composition into a crevice having a width of about 0.2 mm has been reached. The width of 0.2 mm the sulcus crevice is assumed to generally correspond to a healthy gingiva. Therefore it is believed that the invention may provide the potential to effectively perform a gingival retraction for a healthy gingiva. In contrast in the comparative example a penetration of dental composition into the gingival sulcus was only reached with a crevice having a width of about 0.4 mm. Therefore it is believed that the invention may cover a broader range of clinical situations, and may thus also work generally more reliably.

Example 4

A cannula according to an embodiment of the invention (cannula A) and in comparison two differently shaped cannulas (cannulas B and C) were tested in a penetration test to evaluate the impact a penetration of the different cannulas into a gingival sulcus causes to the gingival tissue.

A model of a gingival sulcus was created using a "Heavy Bodied reversible Hydrocolloid Tray Material" lot no.: 012350 from the company DUX Dental, CA, USA. An open plastic container with a generally flat bottom and generally upright sidewalls was provided as cast. The hydrocolloid was heated in accordance with the instructions for use and filled into the cast. After the hydrocolloid had cooled down to room temperature and thus solidified a generally solid block of hydrocolloid had formed. The hydrocolloid block was removed from the cast and placed back reversely into the cast so that the generally flat surface of the block was placed bottom up. In this position the hydrocolloid block was supported by the cast, in particular the upper edges of the block were supported and thus stabilized by the side walls of the cast. A sharp knife was used to cut a slit of about 10 mm depth into the flat surface. The slit in the hydrocolloid block resembles approximately the situation of the gingival sulcus. Therefore the so formed block was used as gingival sulcus model.

Penetration Test:

The gingival sulcus model was placed in a Zwick universal testing machine which was prepared to receive the different cannulas A, B and C in a holder.

Figure 13:
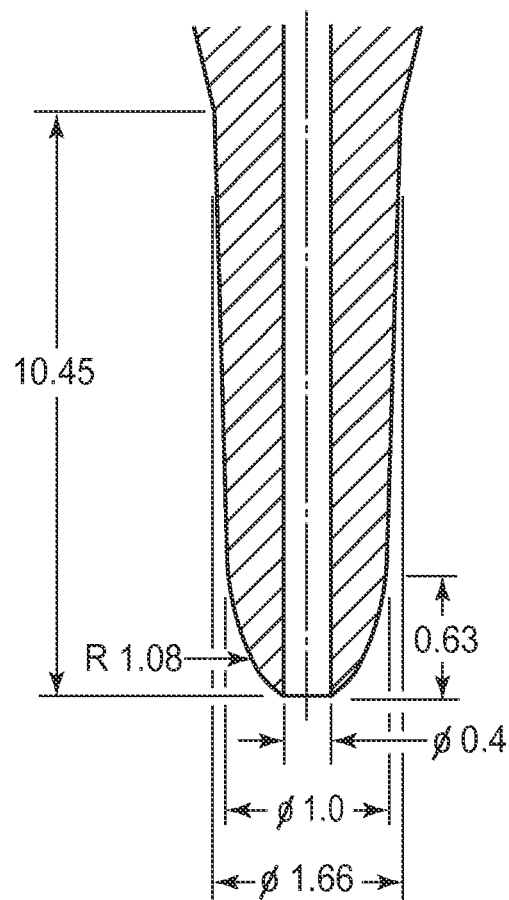
FIG. 13 is a view a cannula shape according to an embodiment of the invention used in Example 4.
Figure 14:
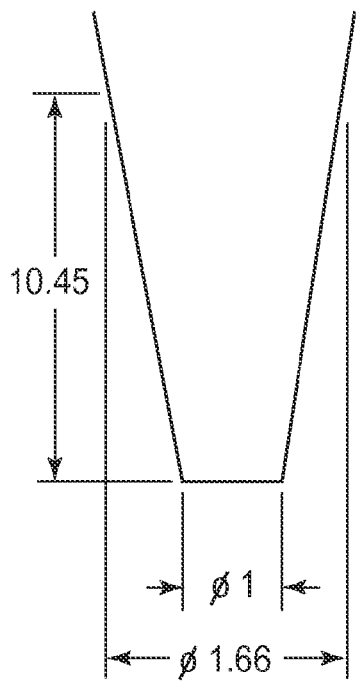
FIGS. 14, 15 are views of two different cannula shapes used in Example 4 relative to the cannula shape shown in FIG. 13.
Figure 15:
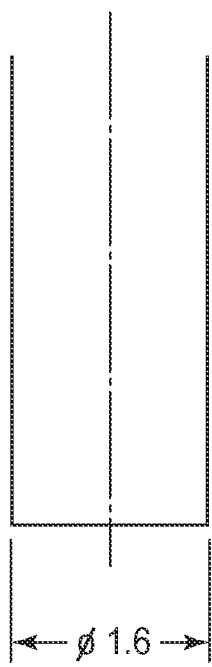

FIG. 13, FIG. 14 and FIG. 15 show the different canulas A, B, and C respectively. Cannula A has a rounded free end which is specifically sized according to an embodiment of the invention. Cannula B has a generally conical shape having similar sizes as cannula A, and cannula C is generally cylindrical having a larger cross-section than cannulas A and B. The shape and cross-section of cannula C corresponds to the shape and cross-section of the prior art cannula according the comparative examples 3.1, 3.2, and 3.3.

The gingival sulcus model was aligned with the slit under the holder so that the cannulas can be moved with their free end leading toward the slit. Each of the cannulas A, B and C were moved at a speed of about 0.25 mm/s into the slit to a penetration depth of about 4 mm. The respective cannulas were refracted from the slit after a time period of about 5 seconds. The model was relocated after test of each of the cannulas so that each cannula penetrated into a fresh section of the slit. Further to reduce impacts from drying of the hydrocolloid the time between cutting of the slit and the penetration test was limited to a maximum of 5 minutes. Further, for the same reason the time between the individual penetration tests with cannulas A, B and C was limited to a maximum of 3 minutes.

The penetration test was repeated with each of the cannulas A, B and C at a second slit cut into the gingival sulcus model.

Figure 16:
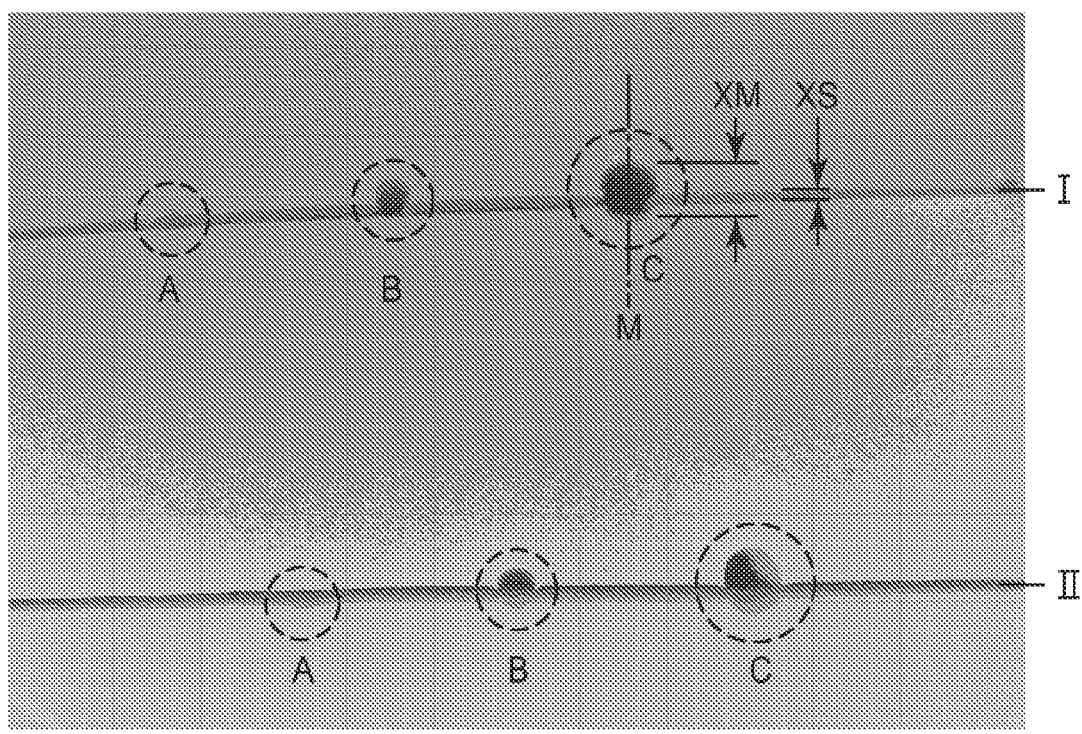
FIG. 16 is a photograph showing the result of the Example 4.

FIG. 16 shows a photograph of the gingival sulcus model used for the penetration test. Two cuts I and II are provided in the model. Further three penetration areas A, B, and C are indicated at each slit I, II. The penetration areas A, B and C exhibit differently sized marks which were caused by the penetration of the respective cannulas, for example by deformation and/or material removal at the edges of the slit. The model was used to measure the penetrations marks left behind from the test.

The method used to measure the size of the penetration mark is explained by example only at penetration area C in slit I (see Figure). The distance XM was measured at the outer edges of the penetration marks on an imaginary line M. The line M is oriented approximately transverse to the slit and extends approximately through the center of the mark. Further the overall width XS of the slit was measured. For determination of the actual size X of the penetration mark the overall width XS was subtracted from the distance XM (X=XM−XS).

Results:

The maximum forces $F_{max}$ applied for moving the cannulas into the slit of the model were measured during the penetration test by use the universal testing machine for each of the cannulas A, B, and C. After the penetration test with all cannulas the surface around the penetration area was evaluated. In particular the sizes of the marks in the gingival sulcus model were measured. The measurements were conducted using a measuring microscope of the type "MM-40" available from Nikon Corp., Japan, including a measuring unit "Quadra-Chek™ 200" available from Metronics Inc., NH, USA. As mentioned the width of the slit outside the penetration areas was measured (XS) to account for an overall widening of the slit resulting from drying of the hydrocolloid material and not resulting from penetration of the cannulas. The measure XS of the general widening was subtracted from the measure XM of the mark. To avoid inacceptable inaccuracies from drying of the hydrocolloid the time between the penetration test and the measurements was limited to a maximum of 10 minutes.

Table 6 shows the measures taken at the model shown in FIG. 16:

| Measurement Series | Cannula Type | Penetration Force $F_{max}$ [N] | Size of mark (Initial measurement) $X_1$ [mm] | Size of mark (Control measurement) $X_2$ [mm] | Average of $X_1$ and $X_2$ = X [mm] |
|---|---|---|---|---|---|
| I | A | 0.30 | 0.21 | 0.23 | 0.22 |
|   | B | 0.76 | 0.65 | 0.60 | 0.63 |
|   | C | 2.17 | 1.40 | 1.40 | 1.40 |
| II | A | 0.29 | 1.39 | 1.39 | 1.39 |
|   | B | 0.91 | 0.81 | 0.80 | 0.81 |
|   | C | 2.23 | 0.29 | 0.30 | 0.30 |

Figure 17:
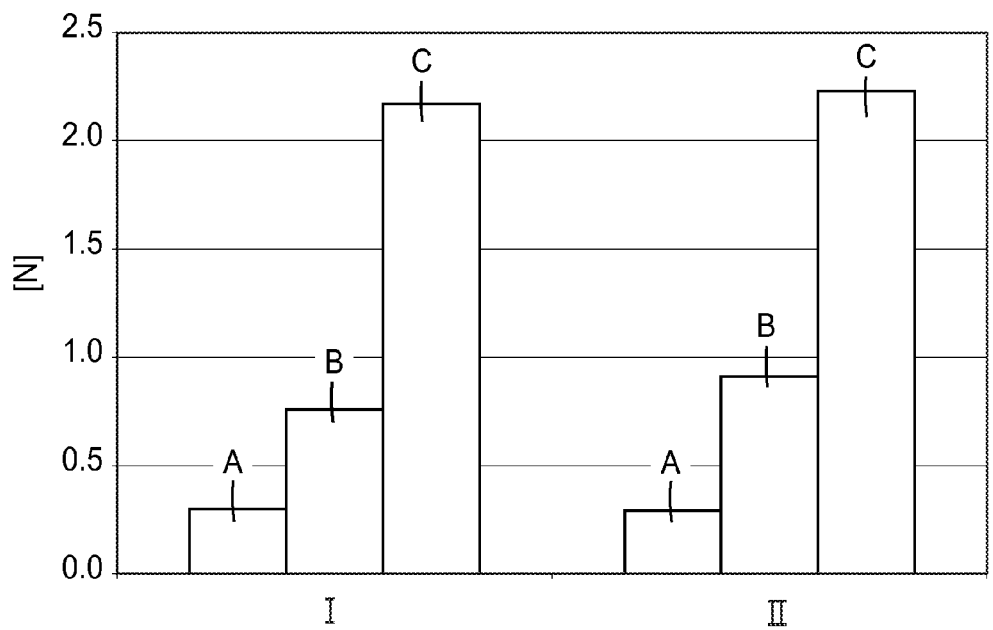
FIGS. 17, 18 are diagrams summarizing the measuring results of the Example 4.
Figure 18:
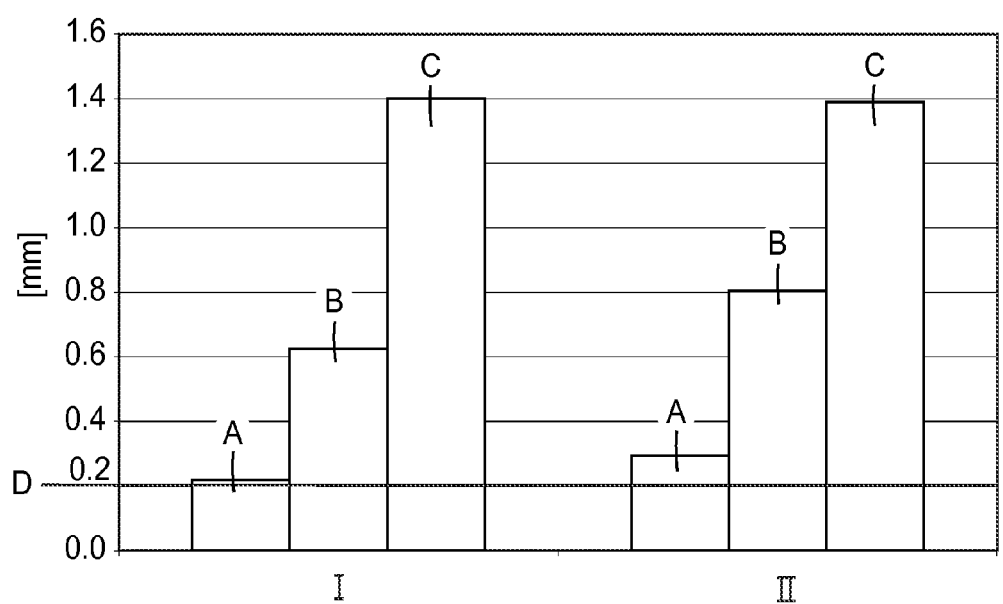

FIG. 17 shows a diagram illustrating the penetration forces as given in table 6, and FIG. 18 shows a diagram illustrating the size of the marks left behind after the penetration test. The bars represent the measurements according to table 6 and are indicated by A, B and C corresponding to the cannula A, B and C, respectively, as used for the test. Further the two groups of bars I and II correspond to the two series of measurements as given in table 6.

Conclusion:

It can be derived from the Example 4 that the cannula of the invention allows a penetration into the gingival sulcus at a relatively low penetration force. Therefore the device of the invention may be relatively convenient in use. Further Example 4 shows that the cannula of the invention may have relatively low impact to the gingival tissue when placed into a gingival sulcus. Therefore the device of the invention may provide for a relatively gentle gingival treatment, and further may provide for relatively low remaining impact in the gingival tissue. The cannula according to the invention may thus overall be suitable for insertion into a gingival sulcus in a patient's mouth.

Example 5

Determination of Storage Modulus of Different Dental Retraction Compositions

The individual components of a dental retraction composition were placed in a speedmixer and mixed for about 60 s at about 2,400 rpm. The mixing process was started immediately after bringing the components in contact. The mixing step was repeated if the obtained paste was cloddy.

The storage modulus was measured using a Physica Rheometer (Paar MCR 300) with plate/plate geometry (diameter of plates: 15 mm; knurled surface). The initial gap was set to 1 mm and is force-operated during the measurement to (1±1) N. The oscillating measurement was performed using a linear ramp from 1 to 10 s$^{-1}$ radial frequency during 300 s. The deflection was set to 0.01%. The storage modulus was determined at 5 s$^{-1}$ radial frequency at room temperature (23° C.).

TABLE 7

| Description | Descriptive Name | Availability |
|---|---|---|
| layer type 1:1 silicate mineral | Kaolin TecFK | Quarzwerke; Frechen |
| layer type 1:2 silicate mineral | Mica SFG70 | Quarzwerke; Frechen |
| astringent | $AlCl_3 * H_2O$ | Aldrich, Fluka |
| retraction paste | Expasyl ™ | Acteon |

TABLE 8

| # | Composition [wt.-%] | content kaolin[1] | content Mica[2] | Extrusion Force [N] | Storage Modulus [kPa] |
|---|---|---|---|---|---|
| 1 | Expasyl (Acteon, Lot No. 4813): |   |   | 185 | 8100 |
| 2 | Kaolin: 4.875 Mica: 60.125 Water: 20 $AlCl_3 * 6H_2O$: 15 | 7.5 | 92.5 | 148 | 3529 |
| 3 | Kaolin: 24 Mica: 39 Water: 22 $AlCl_3 * 6H_2O$: 15 | 38.1 | 61.9 | 114 | 3800 |

[1],[2] with respect to the whole content of silica mineral.

The invention claimed is:

1. A device for use in retracting a gingiva from a human tooth by widening a gingival sulcus with a dental composition, the device comprising:
   a cannula with a free end which comprises an opening for dispensing the dental composition, the free end and the opening being shaped so that the opening can be positioned in the entry of the gingival sulcus with an outer surface of the free end touching the tooth and the gingiva,
   wherein the free end is further shaped so that the gingiva is laterally displaced from the tooth as the cannula is further moved with the opening toward the inside of the gingival sulcus, wherein the cannula comprises:
   a first outer diameter D1 of 0.4 mm, and
   a second outer diameter D2 of 1.0 mm,
   wherein the first outer diameter D1 is located at the front end of the free end, and the second outer diameter D2 is located at a distance L2 from the first outer diameter D1; and
   wherein the distance L2 is 1.0 mm; and
   wherein the first outer diameter D1 is formed by the opening, the opening therefore having a first inner diameter P1 smaller than the outer diameter D1; and
   wherein the outer surface of the free end convexly tapers from the second outer diameter D2 toward the first outer diameter D1, and wherein the convex taper in a direction from D2 toward D1 tapers based on a curve having a radius R which is 3.0 mm; and
   wherein the cannula further has a length L1 between the first outer diameter D1 and a third outer diameter D3; and
wherein the device further comprises:
   a container for receiving the dental composition, the container being in fluid communication with the cannula;
   a piston movable in the container along an extrusion path for advancing the dental composition from the container toward the cannula; and a catch extending laterally to the extrusion path and adapted to catch the device against movement in a direction parallel to the extrusion path; and wherein the device contains a dental composition which comprises:
- a liquid in an amount from 15 wt.-% to 30 wt.-%;
- a layer type 1:1 silicate mineral in an amount from 1 wt.% to 40 wt.-%;
- a layer type 2:1 silicate mineral in an amount from 30 wt.-% to 69 wt.-%;
- an astringent is present in an amount less than 25 wt.-%; and
- additive(s) is present in an amount less than 10 wt.-%;

wt.-% with respect to the whole composition.

2. The device of claim 1, wherein the cannula further has a shaft portion extending between the second outer diameter D2 and the third outer diameter D3, wherein the third outer diameter D3 is between 0.7 mm and 2 mm, and wherein L1 being between 6 mm and 18 mm.

3. The device of claim 1, wherein the cannula comprises a passageway between the opening with the first inner diameter P1 and an inlet with a second inner diameter P2, wherein P2 is between 0.3 and 1.0 mm.

4. The device of claim 1, wherein the cannula has a marking usable as reference with regard to a penetration depth of the cannula in the gingival sulcus, wherein the marking is formed from at least one of a notch, a rim, a printed line, a transition between colors of outside surfaces of the cannula, and a transition between two surface structures of outside surfaces of the cannula.

* * * * *

UNITED STATES PATENT AND TRADEMARK OFFICE
CERTIFICATE OF CORRECTION

PATENT NO. : 8,882,502 B2
APPLICATION NO. : 12/996680
DATED : November 11, 2014
INVENTOR(S) : Helmut Pauser et al.

It is certified that error appears in the above-identified patent and that said Letters Patent is hereby corrected as shown below:

In the specification,

Column 2
Line 26      Delete "US2007259313" and insert -- US2007/259313 --, therefor.

Column 6
Line 12      Delete "volkonskite" and insert -- volkonskoite --, therefor.
Line 37      Delete "ketons" and insert -- ketones --, therefor.
Line 49      Delete "ellag" and insert -- ellagic --, therefor.
Line 50      Delete "potassioum" and insert -- potassium --, therefor.

Column 7
Line 8      Delete "wt. %" and insert -- wt.-% --, therefor.

Column 9
Line 8 (Approx.)      Delete "wt. %" and insert -- wt.-% --, therefor.

Column 11
Line 38      Delete "V." and insert -- 1'. --, therefor.

Column 12
Line 56      Delete "refraction" and insert -- retraction --, therefor.

Column 13
Line 33      Delete "refraction" and insert -- retraction --, therefor.
Line 57      Delete "wt. %" and insert -- wt.-% --, therefor.

Signed and Sealed this
Twenty-first Day of April, 2015

Michelle K. Lee
*Director of the United States Patent and Trademark Office*

CERTIFICATE OF CORRECTION (continued)
U.S. Pat. No. 8,882,502 B2

In the claims,

<u>Column 23</u>
Lines 7-8　　　　In Claim 1, delete "wt. %" and insert -- wt.-% --, therefor.